United States Patent [19]

Carballada et al.

[11] Patent Number: 5,667,771

[45] Date of Patent: *Sep. 16, 1997

US005667771A

[54] RINSE-OFF HAIR CARE COMPOSITIONS USING GRAFTED COPOLYMERS

[75] Inventors: Jose Antonio Carballada; Lauren Ann Thaman; Mario Paul Clarizia, all of Cincinnati, Ohio

[73] Assignee: The Procter & Gamble Company, Cincinnati, Ohio

[*] Notice: The term of this patent shall not extend beyond the expiration date of Pat. No. 5,653,969.

[21] Appl. No.: 621,740

[22] Filed: Mar. 21, 1996

[51] Int. Cl.$^6$ ............................................. A61K 7/06
[52] U.S. Cl. .............................. 424/70.12; 526/279
[58] Field of Search ..................... 424/70.12; 526/279

[56] References Cited

U.S. PATENT DOCUMENTS

| | | | |
|---|---|---|---|
| 3,208,911 | 9/1965 | Oppliger | 167/87 |
| 3,957,970 | 5/1976 | Korkis | 424/70 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 428/352 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,814,402 | 3/1989 | Nakashima et al. | 526/245 |
| 4,902,499 | 2/1990 | Bolich, Jr. et al. | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,166,276 | 11/1992 | Hayama et al. | 525/329 |
| 5,219,560 | 6/1993 | Suzuki et al. | 424/63 |
| 5,229,435 | 7/1993 | Sakai et al. | 523/105 |

FOREIGN PATENT DOCUMENTS

| | | | |
|---|---|---|---|
| 0 117 360 | 12/1983 | European Pat. Off. | A61K 7/06 |
| 0 408 311 A2 | 7/1990 | European Pat. Off. | C08F 230/08 |
| 56-092811 | 7/1981 | Japan | A61K 7/11 |
| 56-129300 | 10/1981 | Japan | A61K 7/06 |
| 4-359912 | 6/1991 | Japan | C08F 299/08 |
| 4-359913 | 6/1991 | Japan | C08F 299/08 |
| 4-360812 | 6/1991 | Japan | A61K 7/00 |
| WO 88/05060 | 7/1988 | WIPO | C08F 30/08 |

*Primary Examiner*—Margaret W. Glass
*Attorney, Agent, or Firm*—Tara M. Rosnell

[57] ABSTRACT

The present invention relates to rinse-off hair care compositions which provide styling and hair conditioning properties without the formation of a non-removable residue. The compositions comprising from about 0.25% to about 70% of a copolymer component having a drying coefficient of less than about 3%; said copolymer component comprising from about 1.5% to 70% of a silicone-grafted adhesive hair styling copolymer having a weight average molecular weight from about 300,000 to about 5,000,000 and from about 30% to about 98.5% of a hydrophobic volatile solvent.

34 Claims, 1 Drawing Sheet

RINSE-OFF HAIR CARE COMPOSITIONS USING GRAFTED COPOLYMERS

TECHNICAL FIELD

The present invention relates to rinse-off hair care compositions containing a hydrophobic silicone grafted copolymer and a hydrophobic, volatile solvent for the copolymer, which deliver the combined conditioning and style retention properties typical of these copolymers without the formation of a non-removable residue on hair shafts. Examples of hair care composition to which this invention relates are hair conditioners, hair styling rinses, rinse-off hair styling mousse and gels, and shampoos useful for cleansing, styling and conditioning the hair.

BACKGROUND OF THE INVENTION

The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration can be accomplished by means of the application of a composition to dampened hair after shampooing and/or conditioning and prior to drying and/or styling. The materials used to provide setting benefits have generally been resins or gums and have been applied in the form of mousses, gels, lotions, or sprays after washing and conditioning the hair. This approach presents several significant drawbacks to the user. It requires a step, in addition to shampooing and/or conditioning, to apply the styling composition. In addition, since the style hold is provided by resin materials which set-up on the hair, the hair tends to feel sticky or stiff after application.

Recently, it has become known to utilize hydrophobic silicone grafted organic backbone copolymers as hair setting agents in rinse-off hair styling/conditioning compositions (e.g., shampoos, rinses, mousses, gels and conditioners). Compositions containing these copolymers provide the combined style retention and conditioning and/or cleansing benefits, without an application step in addition to shampooing/conditioning. These rinse-off styling/conditioning compositions typically comprise a hydrophobic, silicone grafted copolymer solubilized in a suitable hydrophobic, volatile solvent. The hydrophobic copolymer/solvent component deposits on the hair when applied during washing, conditioning or rinsing, but is not readily removed during the final rinsing with water. As the hair is dried, drying or after styling, the volatile solvent evaporates to leave hair treated with the styling/conditioning copolymer.

A hair styling/conditioning copolymer should provide certain styling and conditioning benefits. The copolymer should have sufficient adhesive strength to remain on the hair alter application. The copolymer should have cohesive strength and elasticity properties to provide the ability to style the hair, with or without heated implements, and then to maintain the new hair style. The copolymer should leave hair feeling soft, not as stiff as conventional resins. Such a hair styling copolymer needs to be easily cleaned from the hair (i.e., by shampooing) to prevent a build-up of the copolymer.

Hair care compositions containing various copolymers are well-known in the prior art However, none of these references either teach or suggest compositions having a low visible residue on the hair. See for example, U.S. Pat. No. 3,208,911, to Oppliger, issued Sep. 28, 1965, U.S. Pat. No. 4,601,902, to Fridd et al, issued Jul. 22, 1986, U.S. Pat. No. 4,654,161, to Kollmeier et al., issued Mar. 31, 1987, U.S. Pat. No. 5,106,609, to Bolich hr. et al., issued Apr. 21, 1992, U.S. Pat. No. 4,693,935, to Mazurek, issued Sep. 15, 1997, European Patent Application No. 412,704, to Bolich et al., published Feb. 2, 1991.

It has been observed, however, that hydrophobic, silicone grafted copolymers may be more difficult to remove from the hair by shampooing, than typical hair styling resins and gums. It is often observed, that after repeated cycles of gentle shampooing and towel/air drying, residual styling copolymer can build up on the hair to a point where the residue completely mounds the hair shaft. At this point the residue cannot be removed from the hair with normal shampooing This build-up results in severe cosmetic and comb-ability problems for the user of these hair care products. Without being limited by theory, it is believed that the adhesive strength of the copolymer to the hair is too high relative to the internal cohesive breaking mess. This results in a situation, during gentle washing, in which styling copolymer films fracture and are removed in pieces. Some pieces remain adhered to the hair shaft and are coated with new copolymer during the next application of the composition. The residual pieces act as sites for the formation of the build-up of copolymer.

It has now been found that rinse-off compositions utilizing specifically defined hydrophobic, silicone grafted adhesive hair styling copolymers provide excellent hair conditioning and hair styling properties, and yet are easily removed from the hair by shampooing.

It is an object of the present invention to formulate rinse-off hair care compositions which provide effective hair conditioning and/or cleansing and style retention properties, in which the conditioning and styling copolymer can be easily removed from the hair by shampooing.

It is also an object of the present invention to formulate hair care compositions which provide conditioning and style retention in one produce, in which the conditioning and styling copolymer can be easily removed from the hair by shampooing.

It is a further object of the present invention to provide an improved method for styling and conditioning hair by utilizing a single rinse-off hair care composition.

These and other objects, as may be apparent from the description below, can be obtained by the present invention.

The present rinse-off hair care compositions can comprise, consist of, or consist essentially of any of the required or optional ingredients and/or limitations described herein.

All percentages and ratios are calculated on a weight basis unless otherwise indicated. All percentages are calculated based on total composition unless otherwise indicated.

All ingredient levels refer to the active level of that ingredient, and are exclusive of solvents, by-products, or other impurities that may be present in commercially available sources, unless otherwise indicated.

SUMMARY OF THE INVENTION

The present invention relates to a rinse-off hair care composition comprising:
   A. from about 0.25% to about 70% of a copolymer component having a drying coefficient of less than about 3%, said copolymer component comprising:
      i. from about 1.5% to about 70%, by weight of said copolymer component of a silicone-grafted adhesive hair styling copolymer having a weight average molecular weight from about 300,000 to about 5,000,000, which has a vinyl copolymeric backbone having grafted to it monovalent siloxane copolymeric moieties, said copolymer comprising monomers selected from the group consisting of A monomers, B monomers, C monomers and mixtures thereof;

wherein the weight percent of said copolymer in said rinse-off hair care composition is from about 0.10% to about 7%; and wherein said copolymer is prepared by the polymerization combination of the following relative weight percentages of said A monomers, said B monomers, and said C monomers:

a. from about 45% to about 85% of a hydrophobic, vinyl A monomer, free radically copolymerizable with said B monomers and said C monomers;

b. from 0% to about 5% of a hydrophilic, reinforcing B monomer, copolymerizable with said A monomers and said C monomers, said B monomer being selected from the group consisting of polar monomers and macromers and mixtures thereof; and c. from about 15% to about 50% of a polysiloxane-containing C monomer, copolymerizable with said A monomers and said B monomers, having: a weight average molecular weight of from about 5,000 to about 50,000; and having the general formula:

wherein:

X is a vinyl group copolymerizable with said A monomers and said B monomers;

Y is a divalent linking group;

R is a hydrogen, lower alkyl, aryl or alkoxy;

Z is a monovalent siloxane polymeric moiety having a number average molecular weight of at least about 1500, is essentially unreactive under copolymerization conditions, and is pendant from said vinyl polymeric backbone after polymerization;

n is 0 or 1; and m is an integer from 1 to 3; and wherein said copolymer has an adhesive strength of less than about 30 kg/cm², a cohesive breaking stress of greater than about 20 kg/cm², a cohesive breaking strain of less than about 100%; and wherein the ratio of the cohesive breaking stress to the adhesive strength of said copolymer is greater than or equal to about 1.0; and ii. from about 30% to about 98.5% by weight of said copolymer component of a hydrophobic volatile solvent; and B. from about 30% to about 99.75% of a carrier suitable for application to hair.

DETAILED DESCRIPTION OF THE INVENTION

Figure 1:
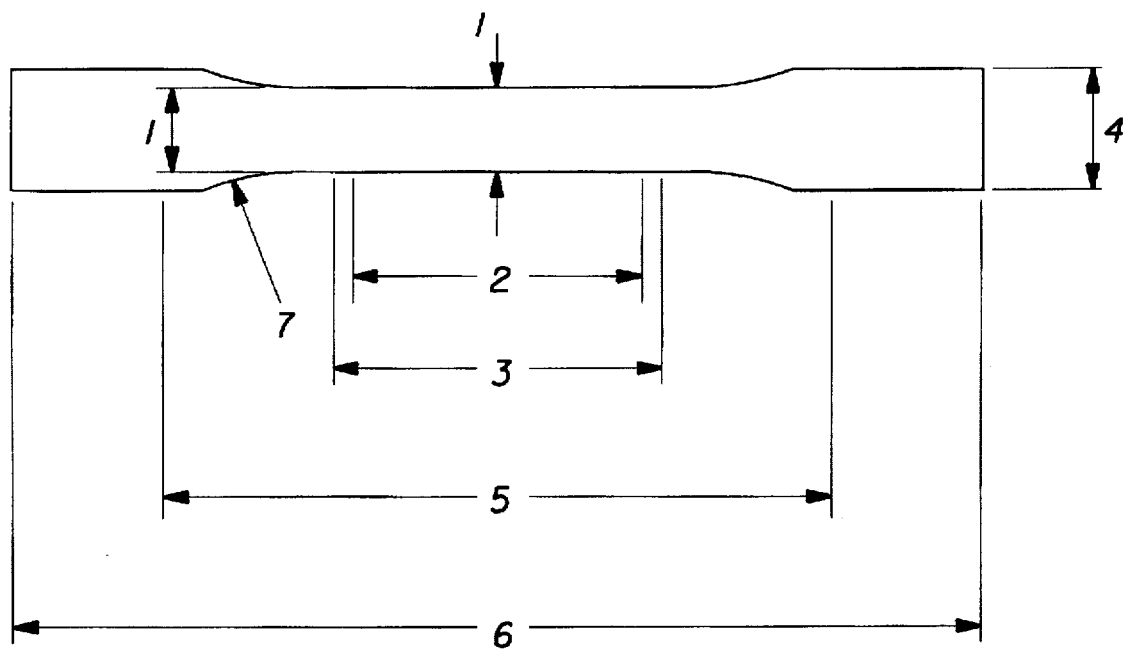
FIG. 1 illustrates an overhead view of a drumbbell-shaped planar copolymer film sample useful for measuring the physical properties of the copolymer, such as the cohesive breaking stress and cohesive breaking strain as described herein.

The essential components of the present invention are described below. Also included is a nonexclusive description of various optional and preferred components useful in embodiments of the present invention.

The hydrophobic copolymers of the present invention can be described as graft copolymers. The term "graft copolymers" is familiar to one of ordinary skill in polymer science and is used herein to describe the copolymers which result by adding or "grafting" a polymeric chemical moiety (i.e. "grafts") onto another polymeric moiety commonly referred to as the "backbone". The backbone typically has a higher molecular weight than the grafts. Thus, graft copolymers can be described as polymers having pendant polymeric side chains, and as being formed from the "grafting" or incorporation of polymeric side chains onto or into a polymer. The polymer to which the grafts are incorporated can be homopolymers or copolymers, e.g. linear random or block polymers. Such polymers are derived from a variety of monomer units.

The term "hydrophobic" is used herein consistent with its standard meaning of lacking affinity for water, whereas "hydrophilic" is used herein consistent with its standard meaning of having affinity for water. As used herein in relation to monomer units and polymeric materials, including the copolymers, and solvents for the copolymers, "hydrophobic" means substantially water insoluble; "hydrophilic" means substantially water soluble. In this regard, "substantially water insoluble" shall refer to a material that is not soluble in distilled (or equivalent) water, at 25° C., at a concentration of 0.2% by weight, and preferably not soluble at 0.1% by weight (calculated on a water pins monomer or polymer weight basis). "Substantially water soluble" shall refer to a material that is soluble in distilled (or equivalent) water, at 25° C., at a concentration of 0.2% by weight, and are preferably soluble at 1.0% by weight. "Soluble" and the like, for purposes hereof, corresponds to the characteristic of a monomer or copolymer, as applicable, to form a homogeneous solution when combined with water or other solvents, as is well understood to those skilled in the art.

The term "rinse-off", as contrasted with the term "leave-on", is used herein to mean that the compositions of the present invention are used in a context whereby the composition is ultimately rinsed or washed from the hair either after or during the application of the product. A "leave-on" product, refers to a hair care composition that is applied to the hair and not further subjected to a rinsing step. Nonlimiting examples of rinse-off products of the present invention include hair conditioners, hair styling rinses, rinse-off hair styling mousse and gels, and shampoos.

The term "suitable for application to human hair" as used herein, means that the compositions or components thereof so described are suitable for use in contact with human hair and the scalp and skin without undue toxicity, incompatibility, instability, allergic response, and the like.

The aforementioned definitions shall also apply to other materials so described herein, to the extent any other definitions regarding such materials are consistent with those stated above.

The compositions of the present invention comprise the following essential components.

Copolymer Component

The rinse-off compositions of the present invention comprise, from about 0.25% to about 70%, preferably from about 4% to about 30%, and more preferably from about 8% to about 18%, by weight of the composition, of a copolymer component. The copolymer component comprises a silicone grafted adhesive hair styling copolymer and a suitable hydrophobic volatile solvent. It is not intended to exclude the use of higher or lower levels of the copolymers, as long as an effective amount is used to provide hair styling and hair conditioning properties to the composition and the composition can be formulated and effectively applied for its intended purpose.

Properties Of The Copolymer Component & Drying Coefficient

The copolymer component of the present invention is also defined by a drying coefficient.

The rate of evaporation of the solvent from the copolymer component is critical to the present invention. The drying coefficient of the copolymer component of the present invention is the degree to which a copolymer component retains its hydrophobic volatile solvent, as it dries. The drying coefficient is determined by filling a dry, weighed 28 in$^2$ Teflon® coated pan with 250 grams of a 5% solution, by weight (i.e. 5% copolymer and 95% solvent) of said copolymer in said hydrophobic volatile solvent of the present invention. The example is dried in a preheated oven or consent temperature chamber at about 140° F. for six days. The drying copolymer component film should be kept in an area protected from air currents, which could result in non-uniform clog. After six days the sample is removed and weighed. The drying coefficient is the calculated percent of the solvent remaining in the sample. In other words:

Drying Coefficient =

$$\left[ 1 - \frac{\text{Weight of Sample at time zero} - \text{Weight of Sample at 6 days}}{0.95 \times (\text{Weight of Sample at time zero} - \text{Tare Weight of the pan})} \right] \times 100\%$$

Silicone Grafted Adhesive Hair Styling Copolymer

The copolymer component of the compositions of the present invention comprises from about 1.5% to about 70%, preferably from about 5.0% to about 40%, more preferably from about 10% to about 25%, by weight of the copolymer component, of a silicone grafted adhesive copolymer. The overall rinse-off hair care composition comprises from about 0.10% to about 7.0%, preferably from about 1.0% to about 4.0%, more preferably from about 1.5% to about 2.5% of the silicone grafted adhesive copolymer. It is not intended to exclude the use of higher or lower levels of the copolymers, as long as an effective amount is used to provide adhesive and film-forming properties to the composition and the composition can be formulated and effectively applied for its intended purpose. By "adhesive" it is meant that when applied as a solution to a surface and dried, the copolymer forms a film which attaches to the surface. Such a film will have adhesive strength, cohesive breaking stress, and cohesive breaking strain.

The silicone grafted adhesive copolymers of the copolymer component of the present invention comprise an organic backbone preferably a carbon backbone derived from ethylenically unsaturated monomers, such as a vinyl polymeric backbone, and a polysiloxane macromer grafted to the backbone. These copolymers are comprised of non-silicone containing, hydrophobic, free radically polymerizable vinyl "A" monomers, copolymerizable with the "B" and/or "C" monomers; grafted polysiloxane-containing vinyl "C" monomers, copolymerizable with "A" and "B" monomers; and, optionally, non-silicone containing, hydrophilic reinforcing "B" monomers which are polymerizable with the "A" and/or "C" monomers.

The silicone grafted copolymers are characterized by polysiloxane moieties covalently bonded to and pendant from a polymeric carbon-based backbone. The backbone will preferably be a carbon chain derived from polymerization of ethylenically unsaturated monomers to which polysiloxane moieties are pendant. The term "ethylenically unsaturated" is used herein to mean a material that contains at least one polymerizable carbon-carbon double bond, which can be mono-, di-, tri, or tetra-substituted. The backbone can also include ether groups, ester groups, amide groups, urethane groups and the like. The polysiloxane moieties can be grafted onto a copolymer backbone or the copolymer can be made by copolymerization of polysiloxane-containing polymerizable monomers at the chain end (e.g., ethylenically unsaturated monomer) with non-polysiloxane-containing copolymerizable monomers. The term "copolymerizable" is used herein to describe a material which can be reacted with another material (e.g. the A monomers, B monomers and C monomers of the present invention) in a polymerization reaction using one or more conventional synthetic techniques, such as ionic, emulsion, dispersion, Ziegler-Natta, free radical, group transfer or step growth polymerization. The preferred copolymerization synthetic technique is free radical polymerization.

The silicone grafted adhesive hair styling copolymer can have a weight average molecular weight of from about 300,000 to about 5,000,000, preferably from about 500,000 to about 2,000,000, more preferably from about 600,000 to about 1,500,000.

Preferably, the adhesive copolymer hereof, when dried to form a film will have a Tg or Tm of at least about −20° C., more preferably at least 25° C. so that they are not unduly sticky, or "tacky" to the touch. As used herein, the abbreviation "Tg" refers to the glass transition temperature of the backbone of the polymer, and the abbreviation "Tm" refers to the crystalline melting point of the backbone, if such a transition exists for a given polymer.

The silicone grafted copolymers of the compositions of the present invention comprise "silicone-containing" (or "polysiloxane-containing") monomers, which form the silicone graft pendant from the backbone, and non-silicone-containing monomers, which form the organic backbone of the polymer.

The silicone grafted copolymers should satisfy the following three criteria:

(1) when dried the copolymer phase-separates into a discontinuous phase which includes the polysiloxane portion and a continuous phase which includes the non-polysiloxane portion;

(2) the polysiloxane portion is covalently bonded to the non-polysiloxane portion; and (3) the number average molecular weight of the polysiloxane-containing C monomer is from about 5,000 to about 50,000.

When used in a composition, such as a rinse-off hair care composition, the non-polysiloxane portion should permit the copolymer to deposit on the hair.

Without being limited by theory, it is believed that the phase separation property provides a specific orientation of the copolymer which results in the desired combination of tactile feel, film-forming or adhesive benefits, and the ability to dry quickly and completely. The phase-separating nature of the compositions of the present invention nay be determined as follows. The copolymer is cast as a solid film out of a solvent (i.e., a solvent which dissolves both the backbone and the polysiloxane-graft portions). This film is then sectioned and examined by transmission electron microscopy. Microphase separation is demonstrated by the observation of inclusions in the continuous phase. These inclusions should have the proper size to match the size of the silicone chain (typically a few hundred nm. or less) and the proper density to match the amount of silicone present. This behavior is well documented in the literature for polymers with this structure (see, for example, S. D. Smith, Ph.D. Thesis, University of Virginia, 1987, and references cited therein).

A second method for determining phase-separating characteristics when silicone containing monomers are used, involves examining the enrichment of the concentration of silicone at the surface of a copolymer film relative to the concentration in the bulk polymer. Since the silicone prefers the low energy air interface, it preferentially orients on the copolymer surface. This produces a surface with the silicone oriented at the surface of the fill. This can be demonstrated experimentally by ESCA (electron spectroscopy for chemical analysis) of the dried film surface. Such an analysis shows a high level of silicone and a greatly reduced level of backbone copolymer when the film surface is analyzed. (Surface here means the first few tens of Angstroms of film thickness.) By varying the angle of the interrogating beam the surface can be analyzed to varying depths.

The copolymers of the present invention am prepared by the polymerization combination of A monomers, C monomers and, if used, B monomers. The silicone grafted copolymers can be synthesized by free radical polymerization of the polysiloxane-containing monomers with the non-polysiloxane-containing monomers. The general principles of free radical polymerization methods are well understood. See, for example, Odian, "Principles of Polymerization", 3rd edition, John Wiley & Sons, 1991, pp. 198–334. The desired A, B, and C monomers are all placed in a reactor, along with a sufficient amount of a mutual solvent so that when the reaction is complete the viscosity of the reaction is reasonable. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to he achieved, typically from a few hours to a few days. The solvent is then removed, usually by evaporation or by precipitating the copolymer by addition of a nonsolvent. The copolymer can be further purified, as desired.

As an alternative to a batch reaction, the copolymer can he made by a semi-continuous or continuous process. In the semi-continuous process, two or more additions of monomers are made during the polymerization reaction. This is advantageous when the copolymer is made of several monomers which react during the polymerization at different tares. The proportions of monomers added to the reaction at the separate points of addition can be adjusted by one of ordinary skill in the art such that the polymers of the final product have a more structure. In other words, the polymers of the final product will have a more consistent monomer content distribution for each of the monomer types charged to the reaction.

Examples of related copolymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference. Additional silicone grafted polymers are also disclosed in U.S. Pat. No. 5,480,634, Hayama et al., issued Oct. 2, 1996, U.S. Pat. No. 5,166,276, Hayama et al., issued Nov. 24, 1992, U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., Mar. 31, 1992, U.S. Pat. No. 5,104,646, Bolich et al., issued Apr. 14, 1992, U.S. Ser. No. 07/758,319, Bolich et al, filed Aug. 27, 1991, and U.S. Ser. No. 07/758,320, Torgerson et al., filed Aug. 27, 1991, all of which are incorporated by reference herein in their entirety.

The particular relative amounts of A monomers, B monomers, and C monomers can way as long as the copolymer backbone is soluble in the hydrophobic, volatile solvent hereof and the silicone grafted copolymer exhibits phase separation when dried.

The copolymers are prepared by the polymerization combination of A monomer, C monomer and, if used, B monomer. The copolymer composition is characterized by the amount of each monomer charged to the polymerization reaction vessel. In general, the silicone grafted, adhesive hair styling copolymer will comprise from about 45% to about 85%, preferably from about 60% to about 85%, more preferably from about 70% to about 80%, most preferably from about 70% to about 75% of the hydrophobic, vinyl A monomer, from 0% to about 5.0%, preferably from 0% to about 3.0% of the hydrophilic, reinforcing B monomer, and from about 15% to about 50%, preferably from about 15% to about 40%, more preferably from about 20% to about 30% of the polysiloxane-containing C monomer. The combination of the A monomers and B monomers preferably comprises from about 50% to about 85%, more preferably about 60% to about 85%, most preferably from about 70% to about 80% of the copolymer.

The hydrophobic vinyl A monomer, which is free radically copolymerizable with B monomers and C monomers, is selected from the group consisting of acrylic acid esters, methacrylic acid esters, vinyl compounds, vinylidene compounds, unsaturated hydrocarbons, $C_1$–$C_{18}$ alcohol esters of organic acids and organic acid anhydrides, and mixtures thereof. Representative examples of hydrophobic vinyl A monomers are acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1--dodecanol, 1-hexadecanol, 1-octa decanol, and the like, the alcohols having from about 1–18 carbon atoms with the number of carbon atoms preferably being from about 1–12; styrene; polystyrene monomer, vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred A monomers include t-butyl acrylate, t-butyl methacrylate, t-butyl styrene, n-butyl methacrylate, isobutyl methacrylate, 2-ethylhexyl methacrylate, methyl methacrylate, and mixtures thereof. Most preferably, A is selected from the group consisting of t-butyl acrylate, t-butyl methacrylate, and mixture thereof.

The hydrophilic, reinforcing B monomer, which is copolymerizable with the A and C monomers, is selected from the group consisting of unsaturated organic mono- and polycarboxylic acids, unsaturated (meth)acrylates, unsaturated (meth)acrylamides, unsaturated (meth)acrylate alcohols, unsaturated aminoalkylacrylates, unsaturated organic acid anhydrides, unsaturated esters of organic acid anhydrides, hydrophilic unsaturated vinyl compounds, hydrophilic unsaturated allyl compounds, hydrophilic unsaturated imides, salts of the foregoing compounds, and mixtures thereof. Representative examples of hydrophilic reinforcing B monomers include acrylic acid, methacrylic acid, N,N-dimethylacrylamide, dimethyl aminoethyl methacrylate, quaternized dimethylaminoethyl methacrylate, methacrylamide, t-butyl acrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines lined above, and mixtures thereof. Preferred B monomers include monomers selected from the group consisting of acrylic acid, methacrylic acid, N,N-dimethyl acrylamide, methacrylamide, t-butyl acrylamide, N-t-butyl acrylamide, dimethylaminoethyl methacrylate, vinyl pyrrolidone, salts thereof and alkyl quaternized derivatives thereof, and mixtures thereof.

The polysiloxane-containing C monomer, copolymerizable with the A and B monomers, is exemplified by the general formula:

$$X(Y)_n Si(R)_{3-m} Z_m$$

wherein X is an ethylenically unsaturated group copolymerizable with the A and B monomers, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 1500, is essentially unreactive under copolymerization conditions, and is pendant from the vinyl polymeric backbone described above; n is 0 or 1; and m is an integer from 1 to 3. The C monomer has a weight average molecular weight from about 5000 to about 50,000, preferably from about 5,000 to about 30,000, more preferably from about 8,000 to about 25,000.

Preferably, the C monomer has a formula selected from the following formulas:

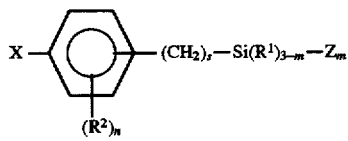

or $$X-CH_2-(CH_2)_s-Si(R^1)_{3-m}-Z_m$$

or

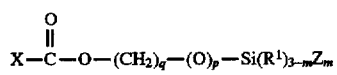

In these structures s is an integer from 0 to about 6, preferably 0, 1, or 2, more preferably 0 or 1; m is an integer from 1 to 3, preferably 1; p is 0 or 1; q is an integer from 2 to 6; $R_2$ is $C_1$–$C_{10}$ alkyl or $C_7$–$C_{10}$ alkylaryl, preferably $C_1$–$C_6$ alkyl or $C_1$–$C_{10}$ alkylaryl, more preferably $C_1$–$C_2$ alkyl; n is an integer from 0 to 4, preferably 0 or 1, more preferably 0; $R^1$ is hydrogen, hydroxyl, lower alkyl, alkoxy, alkylamino, aryl, or alkaryl, preferably $R^1$ is alkyl; X is

$R^3$ is hydrogen or —COOH, preferably $R^3$ is hydrogen; $R^4$ is hydrogen, methyl or —CH$_2$COOH, preferably $R^4$ is methyl; Z is

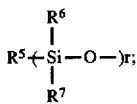

$R^5$, $R^6$, and $R^7$, independently are lower alkyl, alkoxy, alkylamino, aryl, arkaryl, hydrogen or hydroxyl, preferably $R^5$, $R^6$, and $R^7$ are alkyls; and r is an integer of from about 60 to about 700, preferably about 60 to about 400, more preferably r is from about 100 to about 350. Most preferably, $R^5$, $R^6$, and $R^7$ are methyl, p=0, and q=3.

When the C monomer mole weight is less than or equal to about 13,000, preferably from about 8,000 to about 13,000, and r is less than or equal to about 170, preferably from about 100 to about 170, the weight percentage of the C monomer charged to the polymerization process is preferably from about 25% to about 40%, more preferably 25% to about 30%. When the C monomer molecular weight is greater than about 13,000, preferably from about 13,000 to about 50,000, and r is greater than about 170, preferably from about 170 to about 350, the weight percentage of the C monomer charged is preferably from about 20% to about 50%, more preferably 20% to about 30%.

Exemplary silicone grafted polymers for use in the present invention include the following, where the composition of the copolymer is given as weight percentage of each monomer used in the polymerization reaction used to prepare the copolymer.
 (i) 900,000 molecular weight copolymer of 75%/25% charged t-butyl acrylate/polydimethylsiloxane molecular weight about 11,000
 (ii) 900,000 molecular weight copolymer of 80%/20% charged t-butyl acrylate/polydimethylsiloxane molecular weight about 15,000
 (iii) 300,000 molecular weight copolymer of 70%/30% charged t-butyl styrene/polydimethylsiloxane molecular weight about 20,000
 (iv) 700,000 molecular weight copolymer of 67%/3%/30% charged t-butyl acrylate/acrylic acid/polydimethyisiloxane molecular weight about 11,000
 (v) 1,000,000 molecular weight copolymer of 65%35% charged t-butyl acrylate/polydimethylsiloxane molecular weight about 30,000
 (vi) 700,000 molecular weight copolymer of 7%/5%/25% charged t-butyl acrylate/2-ethylhexyl methacrylate/polydimethylsiloxane molecular weight about 15,000.

Hydrophobic Volatile Solvent

The rinse-off hair care products of the present invention also comprise a hydrophobic volatile solvent. By "volatile" it is meant that the useful solvents have a boiling point less than about 225° C. at 760 mm Hg. The hydrophobic, volatile solvent is insoluble in aqueous carriers of the composition. This is determined in the absence of the copolymer, or other emulsifying agents, and can easily be verified by observing whether the solvent and aqueous carrier form separate phases after being mixed at room temperature, as viewed without magnification.

The solvents useful in the present invention generally include hydrophobic, volatile branched hydrocarbons, silicone derivatives, preferably siloxanes, and mixtures thereof. Preferred hydrophobic, volatile branched chain hydrocarbons useful as the solvent herein contain from about 7 to about 14, more preferably from about 10 to about 13, most preferably from about 11 to about 12 carbon atoms. Saturated hydrocarbons are preferred, although it is not intended to exclude unsaturated hydrocarbons. Representative examples of hydrophobic volatile hydrocarbons are Isopar® H and Isopar K® ($C_{11}$–$C_{12}$ isoparaffins), Isopar L® ($C_{11}$–$C_{13}$ isoparaffins), Isopar E® ($C_8$–$C_9$ isoparaffins) and isododecane.

Preferred silicones useful as the volatile hydrophobic solvent herein include volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane, and mixtures thereof. Preferred among the silicones are cyclomethicones, examples of which inlcude octamethyl cyclo tetrasiloxane and decamethyl cyclopentasiloxane, which are commonly referred to D4 and D5 cyclomothicone, respectively.

Properties Of the Copolymers

The copolymers useful in the present invention have specific physical properties as defined by cohesive breaking stress, adhesive strength, cohesive breaking strain and the ratio of the cohesive breaking stress to the adhesive strength.

The silicone grafted adhesive hair styling copolymer of the compositions of the present invention, when dried from the hydrophobic volatile solvent, should meet the following physical parameters: the adhesive strength of the copolymer is less than about 30 kg$_f$/cm$^2$, preferably from about 3 kg$_f$/cm$^2$ to about 20 kg$_f$/cm$^2$, more preferably 5 kg$_f$/cm$^2$ to about 10 kg$_f$/cm$^2$, the cohesive breaking stress of the copolymer component is greater than 20 kg$_f$/cm$^2$, preferably greater than 30 kg$_f$/cm$^2$, more preferably greater than about 70 kg$_f$/cm$^2$; the ratio of the cohesive breaking stress to the adhesive strength of the copolymer component is greater than about 1.0; the cohesive breaking strain of the copolymer is less than about 100%, preferably less than about 70%, more preferably less than about 10%. The term kg$_f$ is a standard physical term denoting kilograms of force adjusted for the gravitational acceleration constant of 9.82 m/s$^2$ (i.e. kg$_f$×9.82 m/s$^2$=1 Newton).

Adhesive Strength

Adhesion is the strength of the bonds formed, upon drying, by a material, (e.g., a copolymer film) to a substrate. The adhesive strength of the copolymer in the copolymer component of the current invention is determined using the following method on human hair. This adhesion method herein is based on Wickett, R. Randal, Sramek, John A. and Trobaugh, Cynthia M., *Measurement of the Adhesive Strength of Hair-Hairspray Junctions*, Journal of the Society of Cosmetic Chemists, Vol. 43, pp. 169–178, Nov./Dec. 1992.

A brass ferrule, or other appropriate holder, is crimped to each end of an undamaged, virgin hair fiber, with an average diameter of from about 80 microns to about 90 microns and a length of about 18 cm. By "virgin hair" is meant that the hair has not been subjected to chemical treatments such as bleaching or perming. The hair fiber can be examined by standard electron microscopic techniques to evaluate the quality of the hair, e.g. the condition of the hair cuticles can be examined.

A ½ inch circular loop, with a single crossover knot, is made in the hair by forming a circle with the hair, then passing one end of the fiber through the circle and pulling the ends until the resultant loop is about ½ inch in diameter. The ends of the hair fiber are then oriented and fixed such that the loop does not contact any surface and such that the plane of the loop is pointed upward with the fiber crossing at the bottom of the loop. The hair fiber is equilibrated for about 24 hours, in a chamber at 75° F. and 50% relative humidity.

Using a microliter syringe, 0.75 microliters of the copolymer component of the invention, is applied to the crossed fibers of the loop to form a bead weld at the crossed fibers. The samples are allowed to dry at 75° F. and 50% relative humidity for 24 hours.

After the bead of copolymer is completely dry, the top of the loop, away from the bead weld, is cut, while handling the samples in such a way as to not put undo stress on the bead weld.

Using the brass ferrules, the hair fiber sample is clamped into a calibrated Instron Model 1122 Tensile Tester. The adhesive strength is determined by stretching the hair fiber at a crosshead speed of 5 mm./min. until the bead weld fails and the hair fibers slip through the weld. After failure, the contact area of the polymer bead and the hair fiber which failed, typically the fiber of smaller diameter, is measured using an optical comparator using standard techniques well known to one of skill in the art of microscopy. The adhesive strength of the copolymer is the measurement of the tensile stress applied to the hair fiber and the weld at the time of failure by the Instron, divided by the polymer to hair contact area which failed.

Cohesive Breaking Stress and Strain

Cohesion is the strength of the bends formed within a sample (e.g., a dried film). The cohesive breaking stress (referred to as tensile strength at break in the ASTM method cited below) is the amount of force required to break a film of copolymer. The strain of the film is a measure of the elasticity of the copolymer film at a given time, i.e., the ratio of the change in length to the original length. The cohesive breaking strain is a measure of the elasticity of the dried film oil the hair at the point of cohesive failure.

The cohesive breaking stress and strain of the copolymer of the compositions of the current invention are determined using the following method. This method is based on ASTM Designation: D 638-91, *Standard Test Method for Tensile Properties of Plastics*, Published January 1992. The following test method to measure cohesive breaking stress and strain is similar to the ASTM standard, however, several modifications are made to better represent the tensile properties of the thin copolymer films achieved on hair. The test method, described herein specifically uses a modified dumbbell shape with a thickness equal to about 1 mm, and uses an Instron Model Mini-55 as the testing machine for applying the force to the polymer film samples.

The cohesive breaking stress and strain measurements can he dependent on the solvent used to form the copolymer film. It is critical to the test method that the specific copolymer component (i.e., styling copolymer and hydrophobic volatile solvent), to be used in the hair care composition, be used.

Figure 2:
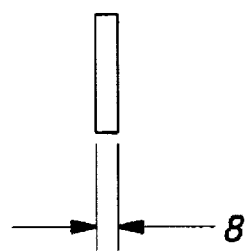
FIG. 2 illustrates a cross-sectional view, showing the thickness of the dumbbell-shaped copolymer film illustrated in FIG. 1.

The copolymer film can be cast directly into the desired dumbbell shape in an appropriately shaped mold. Alternately, when molds are not used, the copolymer film is cut into the dumbbell shape. FIGS. 1 and 2 illustrate the planar dumbbell shaped film to be used in the tensile testing described herein. FIG. 1 illustrates an overhead view of the dumbbell shaped sample. FIG. 2 illustrates a cross section through the dumbbell shaped sample. The width of the narrow section, 1, of the dumbbell is 3 mm. The length of the narrow, 3 mm., section of the dumbbell, 3, is about 15 min. (3=15 mm.). The gauge length of the narrow section, 2, is the initial film length used in the determination of the strain of the sample. The gauge length is equal to or less than the length of the narrow section, preferably equal to the length of the narrow section (i.e., 2=3). If the gauge length is less than the full length of the narrow section, care must be taken measure the change in length of only the gauge length material. The width of the ends of the dumbbell, 4, are about 10 mm. (4=10 mm.). The distance between end sections of the film 5, is about 28 mm. (5=28 mm.). The overall length if the film, 6, is about 64 mm. (6=64 mm.). The length of the wide ends of the film is about 18 mm (6-5)/2=18 mm). The transition sections between the wide ends and the narrow section of the film are about 6.5 mm. in length (i.e. 5-3)/2= 6.5 mm.). Also the end portions of the narrow, center portion should be smoothly curved to avoid any stress points in the sample. The curve of the transition section, should have a radius, 7, of from about 0.5 in. to about 5 inches, and should join tangentially to the narrow section. The film is formed to a thickness, 8, of the 1 mm. (8=1 mm.).

A copolymer film is prepared by drying an amount of the copolymer component, as defined herein (i.e., copolymer and hydrophobic volatile solvent) to form a dry film about 1 mm. thick. The copolymer film is dried at ambient conditions (i.e., 70° F. and 50% relative humidity) until it is fully dry. By "fully dry" it is meant that the dried film contains no more than about 0.05% of the solvent of the component, which is verified by measuring the weight of the copolymer/solvent mixture as a function of time. The drying film should be kept in an area protected from air currents, which could result in non-uniform drying.

The samples are tested on a calibrated Instron Model Mini-55 tensile tester. Before mounting the sample into the Instron, the length, 3, width, 1, and thickness, 8, of the narrow section of the dumbbell shaped sample are measured to the nearest micron with a calibrated micrometer. The dimensional measurements are required by the Instron for stress per unit area calculations. The wide ends of the dumbbell samples are clamped into the Instron and pulled at a crosshead rate of 5 mm. per minute. The Instron tester measures the overall forces (e.g., $kg_f$) applied to the film. These forces are spread over the cross sectional area of the narrow section of the film. The cohesive breaking stress of the copolymer, is the stress applied and measured by the Instron at the point of the failure divided by the cross sectional area of the narrow portion of the film. The cohesive breaking strain of the copolymer, is the ratio of the change in gauge length, 2, (preferably equal to the length, 3), of the narrow portion of the film from the start of the test to failure of the sample to the original gauge length.

Carrier

The rinse-off hair care compositions of the present invention also comprise a carrier, or a mixture of such carriers, which are suitable for application to hair. The carriers are present at from about 30.0% to about 99.75%, preferably from about 70% to about 96%, most preferably from about 82% to about 92%, of the composition. As used herein, the phrase "suitable for application to hair" means that the carrier does not damage or negatively affect the aesthetics of hair or cause irritation to skin.

Hair Conditioners

Where the hair care compositions are condition compositions, the carrier may comprise gel vehicle materials. This gel vehicle comprises two essential components: a lipid vehicle material and a cationic surfactant vehicle material. Cationic surfactant materials are described in detail below. Gel-type vehicles are generally described in the following document: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000— Cetostearyl Alcohol, I. Self Bodying Action", 38 *J. of Colloid and Interface Science* 616–625 (1972).

The gel vehicles may incorporate one or more lipid vehicle materials which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed., 1979). Fatty alcohols included among those useful herein are disclosed in the following documents: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, and Villamarin, et al., issued May 26, 1981. Fatty alcohols are also disclosed in British Specification 1,532,585, published Nov. 15, 1978; and Fukushima, et al., "The Effect of Cetostearyl Alcohol in Cosmetic Emulsions", 98 Cosmetics & Toiletries 89–112 (1983). Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is present at from about 0.1% to about 10.0%, preferably 0.1% to about 5%, of the composition; the cationic surfactant vehicle material is present at from about 0.05% to about 5.0%, preferably 0.1% to about 3%, of the composition.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Preferred vehicles for use in the compositions of the present invention include combinations of hydrophobically-modified hydroxyethyl cellulose materials with thickeners (such as xanthan gum), particular surfactants, quaternary ammonium compounds (such as ditallowdimethyl ammonium chloride). These vehicles are described in detail in U.S. Pat. No. 5,100,658, issued to Bolich, R. E., et al. on Mar. 31, 1992; U.S. Pat. No. 5,104,646, issued to Bolich, R. E., et al. on Apr. 14, 1992; U.S. Pat. No. 5,106,609, issued to Bolich, R. E., et al. on Apr. 21, 1992, all incorporated herein by reference.

Shampoos

When the hair care compositions are shampoo compositions, the carrier may include a surfactant material. The surfactant materials for the shampoo carriers of the invention comprise from about 5% to about 50%, preferably from about 10% to about 30%, most preferably from about 12% to about 25%, of the composition.

Synthetic anionic detergents useful herein, particularly for shampoo compositions, include alkyl and alkyl ether sulfates. These materials have the respective formulae $ROSO_3M$ and $RO(C_2H_4O)_xSO_3M$, wherein R is alkyl or alkenyl of from about 10 to about 20 carbon atom, x is 1 to 10, and M is a water-soluble cation such as ammonium, sodium, potassium and triethanolamine. The alkyl ether sulfates useful in the present invention are condensation products of ethylene oxide and monohydric alcohols having from about 10 to about 20 carbon atoms. Preferably, R has from about 12 to about 18 carbon atoms in both the alkyl and alkyl ether sulfates. The alcohols can he derived from fats, e.g., coconut oil or tallow, or can he synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species, having, for example, an average of 3 moles of ethylene oxide per mole of alcohol, is sulfated and neutralized.

Specific examples of alkyl ether sulfates which may he used in the present invention are sodium coconut alkyl triethylene glycol ether sulfate; sodium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

wherein $R^1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil: sodium or potassium salts of fatty acid amides of methyl tauride in which the fatty acids, for example, are derived from coconut oil. Other anionic synthetic surfactants of this variety are set forth in U.S. Pat. Nos. 2.486.921; 2.486.922; and 2.396.278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid: dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of a-olefins by means of uncomplexed sulfur trioxide, followed by neutralization of the acid reaction mixture in conditions such that any sultones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The a-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene: 1-tetradecene: 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific a-olefin sulfonate mixture of the above type is described more fully in the U.S. Pat. No. 3,332,880, Pflaumer and Kessler, issued Jul. 25, 1967, incorporated herein by reference.

Another class of anionic organic surfactants are the b-alkyloxy alkane sulfonates. These compounds have the following formula:

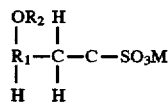

where $R_1$ is a straight chain alkyl group having from about 6 to about 20 carbon atoms, $R_2$ is a lower alkyl group having from about 1 (preferred) to about 3 carbon atoms, and M is a water-soluble cation as herein described.

Specific examples of b-alkyloxy-alkane-1-sulfonates, or alternatively 2-alkyloxy-alkane-1-sulfonates, having low hardness (calcium ion) sensitivity useful herein include: potassium-b-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium b-methoxyoctadecylsulfonate, and ammonium b-n-propoxydodecylsulfonate.

Many additional nonsoap synthetic anionic surfactants are described in McCutcheon's, Detergents and Emulsifiers, 1984 Annual published by Allured Publishing Corporation. Also U.S. Pat. No. 3,929,678, Laughlin et al., issued Dec. 30, 1975, discloses many other anionic as well as other surfactant types and is incorporated herein by reference.

Rinse-off Compositions in General

Nonionic surfactants, which are preferably used in combination with an anionic, amphoteric or zwitterionic surfactant, can he broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may he derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$R_1R_2R_3N \rightarrow O$ wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$RR'R''P \rightarrow O$ wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are; dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, searyldimethylphosphine oxide, cetylethylpropylpbosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chin which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents: M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983 (the U.S. patents being incorporated by reference herein). If included in the compositions of the present invention, the cationic surfactant is present at from about 0.05% to about 5%.

Among the quaternary ammonium-containing cationic surfactant materials useful herein are those of the general formula:

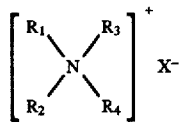

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

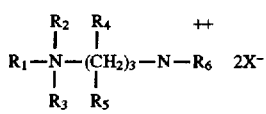

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethyl-ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amine ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include sterylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Zwitterionic surfactants, useful in shampoos as well as conditioners, are exemplified by those which can he broadly described as derivatives of aliphatic quaternary ammonium, phosphonium, and sulfonium compounds, in which the aliphatic radicals can he straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

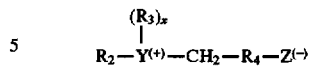

wherein $R_2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R_3$ is an alkyl or monohydroxyalkyl group containing about 1 to about 3 carbon atoms; X is 1 when Y is a sulfur atom, and 2 when Y is a nitrogen or phosphorus atom; $R_4$ is an alkylene or hydroxyalkylene of from about 1 to about 4 carbon atoms and Z is a radical selected from the group consisting of carboxylate, sulfonate, sulfate, phosphonate and phosphate groups.

Examples of such surfactants include:

4-[N,N-di(2-hydroxyethyl)-N-octadecylammnio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines are also useful in the present invention. Examples of lauryl dimethyl carboxymethyl betaine, lauryl dimethyl alphacarboxyethyl betaine, cetyl dimethyl carboxymethyl betaine, lauryl bis-(2-hydroxyethyl) carboxyl betaine, stearyl bis-(2hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydxoxyethyl) sulfopropyl betaine and the like; amidobetaines and amidosulfobetaines, wherein the $RCONH(CH_2)_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sulfates, ethoxylated alkyl sulfates, and mixtures thereof arc preferred for use herein.

The hair care compositions herein can contain a variety of other optional components suitable for rendering such compositions more cosmetically or aesthetically acceptable or to provide them with additional usage benefits. Such conventional optional ingredients are well-known to those skilled in the art. e.g.. pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium sulfate; polyvinyl alcohol; ethyl alcohol; pH adjusting agents, such as citric acid, sodium titrate, succinic acid, phosphoric acid, sodium hydroxide, and sodium carbonate; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and copolymer plasticizing agents, such as glycerin and propylene glycol. Such optional ingredients generally are used individually at levels of from about 0.01% to about 10.0%, preferably from about 0.05% to about 5.0%, of the composition.

Plasticizers

Plasticization of the silicone grafted adhesive hair styling copolymers of the present invention can dramatically hinder the removability of the copolymers with normal shampooing. Without being limited by theory, it is believed that plasticization of the copolymer softens the polymer film on the hair, thereby decreasing the cohesive breaking stress and increasing the cohesive breaking strain of the polymer. This in turn results in the fracturing of the polymer film during shampooing rather than breaking of the adhesive bond to the hair. This results in incomplete removal of the copolymer and an eventual build-up of residue on the hair.

The compositions of the present invention are limited in the amount of materials which act as copolymer plasticizers. In preferred embodiments, the compositions of the present invention should be substantially free of such plasticizing materials, i.e. they should contain less than about 2%, preferably less than about 1%, and more preferably less than about 0.5% of such plasticizer materials. Plasticizing materials are generally relatively non-volatile organic liquids compatible with the copolymer component. By "non-volatile" it is meant that the boiling point of the liquids is greater than or equal to about 260° C. A nonlimiting list of exemplary material which act as plasticizers of the copolymers of the present invention includes diisobutyl adipate, acetyl tri-n-butyl citrate, di(2-ethyl hexyl) azelate, 2-ethyl hexyl diphenyl phosphate, diisoctyl isophthalate, isooctyl benzyl phthalate, butyl stearate, tri-2-ethyl hexyl trimellitate, N-octyl neopentanoate, diisostearyl malate, colloidal fumed silica (such as Cab-O-Sil®, sold by Cabot Corp.) and most perfume materials. Formulation experimentation, is required to determine whether plasticizer levels in the formula impact the adhesive strength, cohesive breaking stress and cohesive breaking strain of the present invention.

pH

The pH of the present compositions should be between about 3 and about 9, preferably between about 4 and about 8.

As with all compositions, the present invention should not contain components which unduly interfere with the performance of the compositions.

The hair care compositions of the present invention can be made using conventional formulation and mixing techniques. Methods of making various types of hair care compositions are described more specifically in the following examples.

METHOD OF USE

The rinse-off hair care compositions of the present invention are used in conventional ways to provide the hair cleaning/conditioning/styling/hold benefits of the present invention. Such methods of use depend upon the type of composition employed but generally involves application of an effective amount of the product to the hair, which is then rinsed from the hair, as in the case of shampoos and conditioner products). By "effective amount" is meant an mount sufficient to provide the hair cleaning/conditioning/styling/hold benefits desired considering the length and texture of the hair, and the type of product used. Typical amounts are generally from about 0.5 g to about 50 g of composition. Preferably, the product is applied to wet or damp hair prior to drying and styling of the hair. After the compositions of the present invention are applied and rinsed from the hair, the hair is dried and styled in the usual ways of the user.

EXAMPLES

The following examples further illustrate produced embodiments within the scope of the present invention. The examples are given solely for the purposes of illustration and are not to be construed as limitations of the present invention as many variations of the invention are possible without departing from its spirit and scope.

Ingredients arc identified by chemical or CTFA name.

The following synthetic procedure is esemplary of the methods useful for synthesizing the copolymers of the present invention.

EXAMPLE 1

Synthesis of Poly(t-butyl acrylate)-graft-polydimethylsiloxane)]

Place 75 parts of t-butyl acrylate and 25 parts of polydimethylsiloxane macromonomer (11,000 MW) (commercially available from 3M, St. Paul, Minn.) in a flask. Add sufficient ethyl acetate as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.25% to about 1.0% by weight relative to the amount of monomer. Heat to 60° C. and maintain this temperature for 48 hours while agitating. Terminate the reaction by cooling to room temperature. The polymer is purified by drying off the reaction solvent in an oven.

By varying the monomers and macromonomers used, the general procedure given above in Example 1, is used to prepare other macromonomers and copolymers of the present invention.

The following Table 1 defines nonlimiting examples of copolymers that can be used in the hair care compositions shown in Examples 2–10. Each of the Examples 2–10 is illustrated with a given copolymer, however, any of the other copolymers from Table 1, or any of orther copolymers of the present invention can be employed. In Table 1, the relative weight percentages of the monomers added to the reaction mix are given.

TABLE 1

The following table defines the silicone copolymers used in the examples (weight ratios given refer to proportion added to reaction mix):

| Copolymer #1 | 75/25 | t-butyl acrylate/polysiloxane-containing C monomer S1 polymer molecular weight about 900,000 |
|---|---|---|
| Copolymer #2 | 80/20 | t-butyl acrylate/polysiloxane-containing C monomer S2 polymer molecular weight about 900,000 |
| Copolymer #3 | 70/30 | t-butyl styrene/polysiloxane-containing C monomer S3 polymer molecular weight about 300,000 |
| Copolymer #4 | 67/3/30 | t-butyl acrylate/acylic acid/ polysiloxane-containing C monomer S1 polymer molecular weight about 700,000 |
| Copolymer #5 | 65/35 | t-butyl acrylate/polysiloxane-containing C monomer S4 polymer molecular weight about 1,000,000 |
| Copolymer #6 | 70/5/25 | t-butyl acrylate/2-ethylhexyl methacrylate/ polysiloxane-containing C monomer S2 polymer molecular weight about 700,000 |

Polysiloxane-containing C monomer S1 has a molecular weight of about 11,000. Polysiloxane-containing C monomer S2 has a molecular weight of about 15,000. Polysiloxane-containing C monomer S3 has a molecular weight of about 20,000. Polysiloxane-containing C monomer S4 has a molecular weight of about 30,000. All polysiloxane-containing C monomers are prepared in a manner similar to silicone grafted monomer exemplified in U.S. Pat. No. 4,728,571, Clemens, issued Mar. 1, 1988, which is incorporated by reference herein in its entirety.

EXAMPLE 2

The following is a hair conditioner composition representative of the present invention.

| Component | Weight % |
|---|---|
| Water | Q.S. to 100% |
| Hydrophobically Modified Hydroxyethylcellulose [1] | 0.25% |
| Stearalkonium Chloride | 0.87% |
| Cetyl Alcohol | 1.85% |
| Stearyl Alcohol | 0.21% |
| Stearamidopropyl Dimethylamine | 0.50% |
| CF1213 ® (Dimethicone Gum) [2] | 2.33% |
| Methylchloroisothiazolinone Methylisothiazolinone | 0.03% |
| Perfume | 0.33% |
| Copolymer #2 | 2.00% |
| SS4230 ® (Trimethylsiloxysilicate) [2] | 0.21% |
| Cyclomethicone D4 | 11.30% |

[1] Polysurf 67 ® supplied by Aqualon
[2] Commercially available from GE

This product is prepared by dissolving the copolymer #2 in Cyclomethicone D4 (solvent). The SS4230® fluid is added to this solution. The other components (except Kathon and perfume) are mixed in a separate vessel at a temperature high enough (80 C.) to melt the solids. The polymer/solvent mixture and the dimethicone gum are added separately to the other components after those have been cooled to at least 45° C. Finally, Kathon and perfume are added, and the product cooled to ambient. This composition is useful for application to the hair to provide conditioning, styling and hold benefits. This copolymer has a cohesive breaking stress of greater than about 20 kg/cm$^2$, an adhesive strength of less than about 30 k/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 3

The following is a hair conditioner composition representative of the present invention.

| Component | Weight % |
|---|---|
| Water | Q.S. to 100% |
| Hydroxyethyl Cellulose | 0.50% |
| Hydrogenated Ditallowdimethyl Ammonium Chloride (Quaternium 18) | 0.85% |
| Cetyl Alcohol | 0.90% |
| Stearyl Alcohol | 0.81% |
| Ceteareth-20 | 0.50% |
| Stearamidopropyl Dimethylamine (Lexamine S13) | 0.22% |
| CF1213 ® (Dimethicone Gum) [1] | 1.33% |
| Methylchloroisothiazolinone Methylisothiazolinone | 0.03% |
| Perfume | 0.33% |
| Copolymer #6 | 2.50% |
| Cyclomethicone D4/D5 Blend [90/10] | 11.30% |

[1] Commercially available from GE

This product is prepared by dissolving the copolymer #6 in Cyclomethicone D4/D5 blend (solvent). The other components (except Kathon and perfume) are mixed in a separate vessel at a temperature high enough (0° C.)) to melt the solids. The polymer/solvent mixture and the dimethicone gum are added separately to the other components after those have been cooled to at least 45° C. Finally, Kathon and perfume are added, and the product is cooled to ambient. This composition is useful for application to the hair to provide conditioning, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 4

The following is a hair shampoo composition representative of the present invention.

| Component | Weight % |
|---|---|
| Water | Q.S. to 100% |
| Ammonium Lauryl Sulfate | 3.14% |
| Ammonium Laureth Sulfate | 13.56% |
| Cetyl Alcohol | 0.45% |
| Stearyl Alcohol | 0.19% |
| Coco Monoethanol Amide | 3.00% |
| Ethylene Glycol Distearate | 2.00% |
| Tricetyl Methyl Ammonium Chloride | 0.50% |
| Methylchloroisothiazolinone Methylisothiazolinone | 0.03% |
| Perfume | 0.20% |
| Copolymer #3 | 4.00% |
| Isododecane | 7.40% |

This product is prepared by dissolving the copolymer #3 in isododecane (solvent). The other components are mixed in a separate vessel at a temperature high enough to melt the solids. The polymer/solvent mixture is added to the other components after those have been cooled. This composition is useful for application to the hair to provide cleansing, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 5

The following is a hair shampoo composition representative of the present invention.

| Component | Weight % |
|---|---|
| Water | Q.S. to 100% |
| Cocoamidopropyl Betaine | 8.30% |
| Ammonium Lauryl Sulfate | 2.12% |
| Ammonium Laureth Sulfate | 6.35% |
| Coco Monoethanol Amide | 1.50% |
| Hydroxypropyl Methocellulose (K15) | 0.25% |
| Ethylene Glycol Distearate | 1.50% |
| Tricetyl Methyl Ammonium Chloride | 0.50% |
| Methylchloroisothiazolinone Methylisothiazolinone | 0.03% |
| Perfume | 0.20% |
| Copolymer #5 | 3.00% |
| Isododecane | 10.00% |

This product is prepared by dissolving the copolymer #5 in isododecane (solvent). The other components are mixed in a separate vessel at a temperature high enough to melt the solids. The polymer/solvent solution is added to the other components after those have been cooled. This composition is useful for application to the hair to provide cleansing, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 6

The following is a rinse-off hair styling gel composition representative of the present invention.

| Component | Weight % |
|---|---|
| Polymer-Solvent Mix | |
| Copolymer #1 | 1.25% |
| Ispar H® [1] | 3.75% |
| Premix | |
| Water | 43.00% |
| Hydrogenated Ditallowdimonium Chloride (Quaternium 18) | 1.00% |
| Main Mix | |
| Water | 50.00% |
| Cabopol 940® | 0.75% |
| Panthenol | 0.05% |
| Perfume | 0.20% |

[1] $C_{11}$-$C_{12}$ Isoparaffin, available from Exxon Chemical Co.

This product is prepared by dissolving the copolymer #1 in Isopar H®. Quaternium 18 is mixed with water at 80° C. The polymer-solvent mixture is added to the Quaternium 18 containing premix at either high or low temperature. The other components are mixed in a separate vessel at ambient temperature. The Quaternium 18 premix with the polymer/solvent mixture is cooled (if needed) and added to the other components. This composition is useful for application to the hair to provide conditioning, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 7

The following is a rinse-off hair spray-on gel composition representative of the present invention.

| Component | Weight % |
|---|---|
| Water | Q.S. to 100% |
| Tallowtrimonium Chloride | 0.10% |
| Hydrogenated Ditallowdimonium Chloride (Quaternium 18) | 0.90% |
| Panthenol | 0.05% |
| Perfume | 0.20% |
| Copolymer #2 | 1.00% |
| Hexamethyl disiloxane | 3.00% |

This product is prepared by dissolving the copolymer #2 in hexamethyl disiloxane (solvent). The other components are mixed in a separate vessel at a temperature high enough (70 C.) to melt the solids. The polymer/solvent solution is added to the other components at either high or low temperature. This composition is useful for application to the hair to provide conditioning, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 8

The following is a hair styling rinse composition representative of the present invention.

| Component | Weight % |
|---|---|
| Premix A | |
| Water | 4.98% |
| Ditallowdimonium Chloride (Varisoft 470) | 1.43% |
| CF1213 ® (Dimethicone Gum) [2] | 2.33% |
| Amodimethicone | 0.10% |
| Premix B | |
| Water | 9.97% |
| Stearalkonium Chloride | 0.30% |
| Panthenol DL | 0.225% |
| Pantyl Ethyl Ether | 0.025% |
| Main Mix | |
| Water | 67.49% |
| Hydrophobically Modified Hydroxyethylcellulose [1] | 1.23% |
| Xanthan Gum | 0.25% |
| Citric Acid | 0.02% |
| Sodium Citrate | 0.09% |
| Cetyl Alcohol | 0.12% |
| Stearyl Alcohol | 0.08% |
| Polymer-Solvent Mixture | |
| Copolymer #1 | 1.75% |
| Cyclomethicone D4/D5 Blend [70/30] | 8.54% |
| SS4230 ® (Trimethylsiloxysilicate) [2] | 0.21% |
| Methylchloroisothiazolinone Methylisothiazolinone | 0.03% |
| Perfume | 0.33% |
| Benzyl Alcohol | 0.50% |

[1] Polysurf 67 ® supplied by Aqualon
[2] Commercially available from GE

This product is prepared by dissolving the copolymer #1 in the cyclomethicone D4/D5 blend (solvent). The SS4236 is added to the polymer solution. Premixes A and B are prepared by combining materials at 70° C. Premix A goes through a colloid mill and is cooled to 38° C. Materials in 'Main Mix', except benzyl alcohol, are mixed at 65° C. The polymer solution is then added to the 'Main Mix'. Main mix goes through a colloid mill and is cooled to 38° C. Premixes and 'Main Mix are combined at 38° C. Then the benzyl alcohol is added. This composition is useful for application to the hair to provide conditioning, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 9

The following is a hair styling rinse composition representative of the present invention.

| Component | Weight % |
|---|---|
| Premix A | |
| Water | 4.67% |
| Ditallowdimonium Chloride (Varisoft 470) | 1.00% |
| Dimethicone Gum (15% in Cyclomethicone D5) [2] | 1.00% |
| Amodimethicone | 0.40% |
| Premix B | |
| Water | 9.36% |
| Stearalkonium Chloride | 0.15% |
| Panthenol DL | 0.225% |
| Pantyl Ethyl Ether | 0.025% |
| Main Mix | |
| Water | 63.53% |
| Hydrophobically Modified Hydroxyethylcellulose [1] | 1.00% |
| Xanthan Gum | 0.10% |
| Citric Acid | 0.02% |
| Sodium Citrate | 0.09% |
| Cetyl Alcohol | 0.60% |
| Stearyl Alcohol | 0.40% |
| Polymer-Solvent Mixture | |
| Copolymer #4 | 2.50% |
| Cyclomethicone D4/D5 Blend [95/5] | 14.17% |
| Methylchloroisothiazolinone Methylisothiazolinone | 0.03% |
| Perfume | 0.33% |
| Benzyl Alcohol | 0.50% |

[1] Polysurf 67 ® supplied by Aqualon
[2] Commercially available from GE

This product is prepared by dissolving the copolymer #4 in the cyclomethicone D4/D5 blend (solvent). Premixes A and B are prepared by combining materials at 70° C. Premix A goes through a colloid mill and is cooled to 38° C. Materials in Main Mix, except benzyl alcohol, are mixed at 65° C. The polymer solution is added to the Main Mix. Main mix goes through a colloid mill and is cooled to 38° C. Premixes and Main Mix are combined at 38° C. Then the benzyl alcohol is added. This composition is useful for application to the hair to provide conditioning styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

EXAMPLE 10

The following is a rinse-off hair styling mousse composition representative of the present invention.

| Component | Weight % |
|---|---|
| Water | Q.S. to 100% |
| Tallowtrimonium Chloride | 0.10% |
| Hydrogenated Ditallowdimonium Chloride (Quaternium 18) | 0.90% |
| Lauramine Oxide | 0.20% |
| Panthenol | 0.05% |
| Perfume | 0.20% |
| Copolymer #2 | 1.00% |
| Hexamethyl disiloxane | 3.00% |
| Isobutane | 7.00% |

This product is prepared by dissolving the copolymer #2 in hexamethyl disiloxane (solvent). The other components (except isobutane) are mixed in a separate vessel at a temperature high enough (70° C.) to melt the solids. The polymer/solvent solution is added to the other components after those have been cooled. Aluminum aerosol cans are then filled with 95 parts of this batch, affixed with a valve which is crimped into position, and lastly pressure filled with 5 parts Isobutane. This composition is useful for application to the hair to provide conditioning, styling and hold benefits. This copolymer has a cohesive breaking stress of greater than about 20 kg/cm$^2$, an adhesive strength of less than about 30 kg/cm$^2$, a cohesive breaking strain of less than about 100%, and a ratio of cohesive breaking stress to adhesive strength greater than or equal to 1. The copolymer component described in this example has a drying coefficient of less than about 3%.

When the compositions defined in Examples II-X are applied to hair in the conventional manner, they provide effective hair conditioning and styling/hold benefits without leaving the hair with a sticky/stiff feel.

What is claimed is:

1. A rinse-off hair care composition comprising:
   A. from about 0.25% to about 70%, by weight of the rinse-off hair care composition, of a copolymer component comprising:
      i. from about 1.5% to about 70%, by weight of said copolymer component, of a silicone-grafted adhesive hair styling copolymer having a weight average molecular weight from about 300,000 to about 5,000,000, which has a vinyl polymeric backbone having grafted to it monovalent siloxane polymeric moieties, said copolymer comprising monomers selected from the group consisting of A monomers, B monomers, C monomers and mixtures thereof, wherein the weight percent of said copolymer in said rinse-off hair care composition is from about 0.1 to about 7%; and wherein said copolymer is prepared by the polymerization combination of the following relative weight percentages of said A monomers, said B monomers, and said C monomers:
         a. from about 45% to about 85%, by weight of said copolymer, of a hydrophobic, vinyl A monomer, free radically copolymerizable with said B monomers and said C monomers;
         b. from 0% to about 5%, by weight of said copolymer, of a hydrophilic, reinforcing B monomer, copolymerizable with said A monomer and said C monomer, said B monomer being selected from the group consisting of polar monomers and macromers and mixtures thereof; and
         c. from about 25% to about 50%, by weight of said copolymer, of a polysiloxane-containing C monomer, copolymerizable with said A monomer and said B monomer, said C monomer having a weight average molecular weight of from about 5,000 to about 13,000; and having the general formula:

$X(Y)_nSi(R)_{3-m}(Z)_m$ 

wherein:
         X is a vinyl group copolymerizable with said A monomers and said B monomers;
         Y is a divalent linking group;
         R is a hydrogen, lower alkyl, aryl or alkoxy;
         Z is a monovalent siloxane polymeric moiety having a number average molecular weight of at least about 1500, is essentially unreactive under copolymerization conditions, and is pendant from said vinyl polymeric backbone after polymerization;
         n is 0 or 1; and
         m is an integer from 1 to 3; and
         wherein said copolymer has an adhesive strength of less than about 30 kg/cm$^2$; a cohesive breaking stress of greater than about 20 kg/cm$^2$, a cohesive breaking strain of less than about 100%; and wherein the ratio of the cohesive breaking stress to the adhesive strength of said copolymer is greater than or equal to about 1.0; and
      ii. from about 30% to about 98.5%, by weight of said copolymer component, of a hydrophobic volatile solvent; and
   B. from about 30% to about 99.75%, by weight of the rinse-off hair care composition, of a carrier suitable for application to hair.

2. A rinse-off hair care composition according to claim 1 wherein said hydrophobic, vinyl A monomer is selected from the group consisting of acrylic acid esters, methacrylic acid esters, vinyl compounds, vinylidene compounds, unsaturated hydrocarbons, $C_1$–$C_{18}$ alcohol esters of organic acids and organic acid anhydrides, and mixtures thereof.

3. A rinse-off hair care composition according to claim 1 wherein said hydrophobic, vinyl A monomer is selected from the group consisting of t-butyl acrylate, t-butyl methacrylate, t-butyl styrene, and mixtures thereof.

4. A rinse-off hair care composition according to claim 2 wherein said hydrophilic, reinforcing B monomer is selected from the group consisting of unsaturated organic mono- and polycarboxylic acids, unsaturated (meth)acrylates, unsaturated (meth)acrylamides, unsaturated (meth)acrylate alcohols, unsaturated aminoalkylacrylates, unsaturated organic acid anhydrides, unsaturated esters of organic acid anhydrides, hydrophilic unsaturated vinyl compounds, hydrophilic unsaturated allyl compounds, hydrophilic unsaturated imides, salts of the foregoing compounds, and mixtures thereof.

5. A rinse-off hair care composition according to claim 2 wherein said hydrophilic, reinforcing B monomer is selected from the group consisting of acrylic acid, N,N-dimethyl acrylamide, dimethylaminoethyl methacrylate, quaternized dimethylaminoethyl methacrylate, t-butyl acrylamide, vinyl pyrrolidone, salts of acids and amines listed above, and mixtures thereof.

6. A rinse-off hair care composition according to claim 4 wherein said polysiloxane-containing C monomer has a formula selected from the following group:

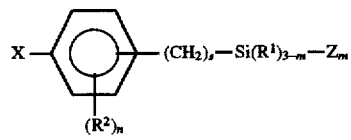

or

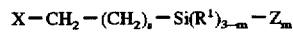

or

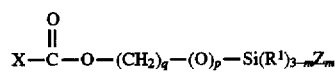

wherein s is 0, 1, 2, 3, 4, 5 or 6; m is 1, 2 or 3; p is 0; q is 2, 3, 4, 5 or 6; $R^1$ is hydrogen, hydroxyl, lower alkyl, alkoxy, alkylamino, aryl, or alkaryl; $R^2$ is C1–C6 alkyl or C7–C10 alkylaryl; n is 0, 1, 2, 3 or 4; X is

whereto $R^3$ is hydrogen or —COOH; $R^4$ is hydrogen, methyl or —CH$_2$COOH; Z is

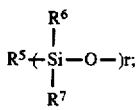

$R^5$, $R^6$, and $R^7$ independently are lower alkyl, alkoxy, alkylamino, aryl, arkaryl, hydrogen or hydroxyl; and r is an integer of from about 100 to about 170.

7. A rinse-off hair care composition according to claim 4 wherein said polysiloxane-containing C monomer has a formula of:

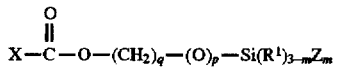

wherein m is 1; p is 0; q is 3; $R^1$ is methyl; X is

wherein $R^3$ is hydrogen; $R^4$ is methyl; and Z is

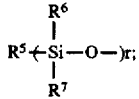

$R^5$, $R^6$, and $R^7$ are all methyl; and r is an integer of from about 100 to about 170.

8. A rinse off hair care composition according to claim 6 wherein said hydrophilic volatile solvent is selected from the group consisting of hydrophobic, volatile $C_7$–$C_{14}$ branched hydrocarbons, hydrophobic, volatile silicones and mixtures thereof.

9. A rinse off hair care composition according to claim 6 wherein said hydrophilic volatile solvent is selected from the group consisting of isododecane, cyclomethicone and mixtures thereof.

10. A rinse off hair care composition according to claim 8 wherein said copolymer component has a drying coefficient of less than about 2%; and said copolymer has an adhesive strength of from about 3 kg/cm² to about 20 kg/cm²; a cohesive breaking stress of greater than about 30 kg/cm², and a cohesive breaking strain of less than about 70%.

11. A rinse-off hair care composition according to claim 8 wherein said copolymer component has a drying coefficient of less than about 0.5%; and said copolymer has an adhesive strength of from about 5 kg/cm² to about 10 kg/cm²; a cohesive breaking stress of greater than about 70 kg/cm², and a cohesive breaking strain of less than about 10%.

12. A rinse-off hair care composition according to claim 10 wherein said carrier comprises a shampoo which additionally comprises from about 10% to about 30% of a synthetic surfactant.

13. A rinse-off hair care composition according to claim 12 wherein said synthetic surfactant is selected from the group consisting of alkyl sulfates, ethoxylated alkyl sulfates, and mixtures thereof.

14. A rinse-off hair care composition according to claim 10 wherein said carrier comprises a conditioner which further comprises:

A. from about 0.1% to about 10% of a lipid vehicle material; and

B. from about 0.05% to about 5% of a cationic surfactant.

15. A rinse-off hair care composition according to claim 14 wherein said cationic surfactant is a quaternary ammonium surfactant.

16. A rinse-off hair care composition according to claim 15, wherein said lipid vehicle material is selected from the group consisting of cetyl alcohol, stearyl alcohol, cetyl palmitate, glyceryl monostearate, and mixtures thereof.

17. A method for delivering both hair conditioning and hair style retention to human hair by administering a safe and effective amount of the composition of claim 3 to a human in need of such treatment.

18. A rinse-off hair care composition comprising:

A. from about 0.25% to about 70%, by weight of the rinse-off hair care composition, of a copolymer component comprising:

i. from about 1.5% to about 70%, by weight of said copolymer component, of a silicone-grafted adhesive hair styling copolymer having a weight average molecular weight from about 300,000 to about 5,000,000, which has a vinyl polymeric backbone having grafted to it monovalent siloxane polymeric moieties, said copolymer comprising monomers selected from the group consisting of A monomers, B monomers, C monomers and mixtures thereof; wherein the weight percent of said copolymer in said rinse-off hair care composition is from about 0.10% to about 7%; and wherein said copolymer is prepared by the polymerization combination of the following relative weight percentages of said A monomers, said B monomers, and said C monomers:

a. from about 45% to about 85%, by weight of said copolymer, of a hydrophobic, vinyl A monomer, free radically copolymerizable with said B monomers and said C monomers;

b. from 0% to about 5%, by weight of said copolymer, of a hydrophilic, reinforcing B monomer, copolymerizable with said A monomer and said C monomer, said B monomer being selected from the group consisting of polar monomers and macromers and mixtures thereof; and c. from about 15% to about 50%, by weight of said copolymer, of a polysiloxane-containing C monomer, copolymerizable with said A monomer and said B monomer, said C monomer having a weight average molecular weight of from about 13,000 to about 50,000; and having the general formula:

wherein:

X is a vinyl group copolymerizable with said A monomers and said B monomers;

Y is a divalent linking group;

R is a hydrogen, lower alkyl, aryl or alkoxy;

Z is a monovalent siloxane polymeric moiety having a number average molecular weight of at least about 1500, is essentially unreactive under copolymerization conditions, and is pendant from said vinyl polymeric backbone after polymerization;

n is 0 or 1; and m is an integer from 1 to 3; and wherein said copolymer has an adhesive strength of less than about 30 kg/cm²; a cohesive breaking stress of greater than about 20 kg/cm², a cohesive breaking strain of less than about 100%; and wherein the ratio of the cohesive breaking stress to the adhesive strength of said copolymer is greater than or equal to about 1.0; and ii. from about 30% to about 98.5%, by weight of said copolymer component, of a hydrophobic volatile solvent; and B. from about 30% to about 99.75%, by weight of the rinse-off hair care composition, of a carrier suitable for application to hair.

19. A rinse-off hair care composition according to claim 18 wherein said hydrophobic, vinyl A monomer is selected from the group consisting of acrylic acid esters, methacrylic acid esters, vinyl compounds, vinylidene compounds, unsaturated hydrocarbons, $C_1$–$C_{18}$ alcohol esters of organic acids and organic acid anhydrides, and mixtures thereof.

20. A rinse-off hair care composition according to claim 18 wherein said hydrophilic, vinyl A monomer is selected from the group consisting of t-butyl acrylate, t-butyl methacrylate, t-butyl styrene, and mixtures thereof.

21. A rinse-off hair care composition according to claim 19 wherein said hydrophilic, reinforcing B monomer is selected from the group consisting of unsaturated organic mono- and polycarboxylic acids, unsaturated (meth)acrylates, unsaturated (meth)acrylamides, unsaturated (meth)acrylate alcohols, unsaturated aminoalkylacrylates, unsaturated organic acid anhydrides, unsaturated esters of organic acid anhydrides, hydrophilic unsaturated vinyl compounds, hydrophilic unsaturated allyl compounds, hydrophilic unsaturated imides, salts of the foregoing compounds, and mixtures thereof.

22. A rinse-off hair care composition according to claim 19 wherein said hydrophilic, reinforcing B monomer is selected from the group consisting of acrylic acid, N,N-dimethyl acrylamide, dimethylaminoethyl methacrylate, quaternized dimethylaminoethyl methacrylate, t-butyl acrylamide, vinyl pyrrolidone, salts of acids and amines listed above, and mixtures thereof.

23. A rinse-off hair care composition according to claim 21 wherein said polysiloxane-containing C monomer has a formula selected from the following group:

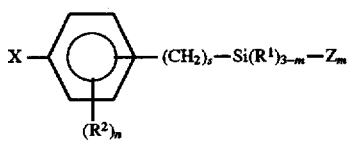

or

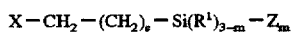

or

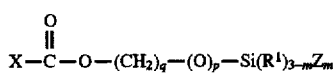

wherein s is 0, 1, 2, 3, 4, 5 or 6; m is 1, 2 or 3; p is 0; q is 2, 3, 4, 5 or 6; $R^1$ is hydrogen, hydroxyl, lower alkyl, alkoxy, alkylamino, aryl, or alkaryl; $R^2$ is C1–C6 alkyl or C7–C10 alkylaryl; n is 0, 1, 2, 3 or 4; X is

wherein $R^3$ is hydrogen or —COOH; $R^4$ is hydrogen, methyl or —CH$_2$COOH; Z is

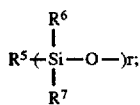

$R^5$, $R^6$, and $R^7$ independently are lower alkyl, alkoxy, alkylamino, aryl, arkaryl, hydrogen or hydroxyl; and r is an integer of from about 170 to about 350.

24. A rinse-off hair care composition according to claim 21 wherein said polysiloxane-containing C monomer has a formula of:

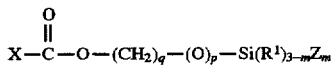

wherein m is 1; p is 0; q is 3; $R^1$ is methyl; X is

wherein $R^3$ is hydrogen; $R^4$ is methyl; and Z is

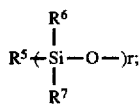

$R^5$, $R^6$, and $R^7$ are all methyl; and r is an integer of from about 170 to about 350.

25. A rinse off hair care composition according to claim 23 wherein said hydrophilic volatile solvent is selected from the group consisting of hydrophobic, volatile $C_7$–$C_{14}$ branched hydrocarbons, hydrophobic, volatile silicones and mixtures thereof.

26. A rinse off hair care composition according to claim 23 wherein said hydrophilic volatile solvent is selected from the group consisting of isododecane, cyclomethicone and mixtures thereof.

27. A rinse-off hair care composition according to claim 25 wherein said copolymer component has a drying coefficient of less than about 2%; and said copolymer has an adhesive strength of from about 3 kg/cm² to about 20 kg/cm$_2$; a cohesive breaking stress of greater than about 30 kg/cm², and a cohesive breaking strain of less than about 70%.

28. A rinse-off hair care composition according to claim 25 wherein said copolymer component has a drying coefficient of less than about 0.5%; and said copolymer has an adhesive strength of from about 5 kg/cm² to about 10 kg/cm²; a cohesive breaking stress of greater than about 70 kg/cm², and a cohesive breaking strain of less than about 10%.

29. A rinse-off hair care composition according to claim 27 wherein said carrier comprises a shampoo which additionally comprises from about 10% to about 30% of a synthetic surfactant.

30. A rinse-off hair care composition according to claim 29 wherein said synthetic surfactant is selected from the group consisting of alkyl sulfates, ethoxylated alkyl sulfates, and mixtures thereof.

31. A rinse-off hair care composition according to claim 27 wherein said carrier comprises a conditioner which additionally comprises:

A. from about 0.1% to about 10% of a lipid vehicle material; and

B. from about 0.05% to about 5% of a cationic surfactant.

32. A rinse-off hair care composition according to claim 31 wherein said cationic surfactant is a quaternary ammonium surfactant.

33. A rinse-off hair care composition according to claim 32 wherein said lipid vehicle material is selected from the group consisting of cetyl alcohol, stearyl alcohol, cetyl palmitate, glyceryl monostearate, and mixtures thereof.

34. A method for delivering both hair conditioning and hair style retention to human hair by administering a safe and effective amount of the composition of claim 18 to a human in need of such treatment.

* * * * *